United States Patent [19]
Fodge et al.

[11] Patent Number: 5,476,775
[45] Date of Patent: Dec. 19, 1995

[54] HEMICELLULASE ACTIVE AT PH AND TEMPERATURE EXTREMES

[75] Inventors: Douglas W. Fodge; David M. Anderson, both of Rockville; Thomas M. Pettey, Gaithersburg, all of Md.

[73] Assignee: Chemgen Corporation, Gaithersburg, Md.

[21] Appl. No.: 851,122

[22] Filed: Mar. 16, 1992

Related U.S. Application Data

[63] Continuation of Ser. No. 529,655, May 29, 1990, abandoned.

[51] Int. Cl.$^6$ .............................. C12N 9/00; C12N 9/42
[52] U.S. Cl. ............................................ 435/209; 435/183
[58] Field of Search ..................................... 435/183, 209

[56] References Cited

U.S. PATENT DOCUMENTS

| | | | |
|---|---|---|---|
| 3,615,721 | 10/1971 | Silberman | 99/199 |
| 3,640,723 | 2/1972 | Uhlig et al. | 99/9 |
| 4,033,415 | 7/1977 | Holtmyer et al. | 166/308 |
| 4,368,136 | 1/1983 | Murphey | 262/316 |
| 4,388,330 | 6/1983 | Wobben et al. | 426/599 |
| 4,639,375 | 1/1987 | Tsai | 426/49 |

FOREIGN PATENT DOCUMENTS

| | | | |
|---|---|---|---|
| 0285098 | 3/1988 | European Pat. Off. | A23K 1/14 |
| PCT/GB85/ 00100 | 3/1985 | WIPO | C12P 19/14 |

OTHER PUBLICATIONS

Akino et al. Chem. Abstracts 107 (11):95233t Appl. Microbiol. Biotechnol. 26(4), 323–7, (1987).
Akino et al. Agric. Biol. Chem 52(3), 773–779 (1988).
EMI et al., *Crystallization and Some Properties of Mannanase*, Agr. Biol. Chem., vol. 36, No. 6, pp. 991–1001 (972).
Methods in Enzymology, vol. 160 (Academic Press 1988), pp. 10–19.
Ebisu et al., "Conserved structures of cell wall protein genes among protein–producing *Bacillus brevis* strains," J. Bacteriol. 173(3): 1312–1320 (1990).
A. Araujo and O. P. Ward, "Hemicellulases of Bacillus species: preliminary comparative studies on production and proterties of mannanases and galactanases," J. Applied Baceriol. 68:253–261 (1990).
Almin et al., "Extracellular enzyme system utilized by the Fungus *Sporotrichum pulverulentum* (*Chrysosporium lignorum*) for the breakdown of cellulose," Eur. J. Biochem. 51:207–211 (1975).
Almin and Eriksson, "Enzymic degradation of polymers, II. Viscometric determination of cellulase activity in absolute terms," Biochim. Biophys. Acta 139:248–253 (1967).
Almin and Eridsson, "Enzymic degration of polymers, I. Viscometric method for the determination of enzymic activity," Biochim. Biophys. Acta 139:238–247 (1967).
Methods in Enzymology, vol. 160 (Academic Press 1988), pp. 522–633.
Esteban et al., "B–D–Xylanases of *Bacillus circulans* WL–12," Can. J. Microbiol. 28:733–739 (1982).
Hansen et al., "Alginase enzyme production of *Bacillus circulans*," Appl. Environ. Microbiol. 47(4):704–709 (1984).
Matsudaira, P., "Sequence from picomole quantities of proteins electroblotted onto polyvinylidene difluoride membranes," J. Biol. Chem. 262:10035–38 (1987).
Methods in Enzymology, vol. 160, (Academic Press 1988), pp. 368–377.
Methods in Enzymology vol. 160, (Academic Press 1988), pp. 180–187.

*Primary Examiner*—Margaret Parr
*Assistant Examiner*—David Schreiber
*Attorney, Agent, or Firm*—Foley & Lardner

[57] ABSTRACT

Soil bacteria can be isolated which produce an enzyme capable of catalyzing the degradation of mannan-containing hemicellulose under conditions combining high pH and high temperature. Such bacteria can be cultured or used as sources of genetic information with which to engineer other microorganisms to produce the enzyme. Commercially useful quantities of native or recombinant hemicellulase can thus be produced by cultures consisting essentially of microorganisms capable of producing the enzyme.

2 Claims, 4 Drawing Sheets

HEMICELLULASE ACTIVE AT PH AND TEMPERATURE EXTREMES

This application is a continuation of application Ser. No. 07/529,655, filed May 29, 1990 now abandoned.

BACKGROUND OF THE INVENTION

Different enzymes are categorized as a specific type of hemicellulase—a glucanase, a xylanase or a mannanase, for example—based on an ability to catalyze the hydrolysis of heteropolysaccharides composed of glucan, xylan or mannan, respectively. It is known that enzymes that effect hydrolysis of mannans, such as a galactan or a glucomannan, are produced by various microorganisms, including bacteria and fungi, and that they also occur in some animals and in numerous plants. Among the microorganisms that produce such mannanases are species of Aeromonas, Aspergillus, Streptomyces, Rhodococcus and Bacillus. See 160 METHODS IN ENZYMOLOGY Part A, Sect. II (1988).

Hemicellulases have been employed commercially, for example, in the processing of coffee, chocolate, cocoa, tea and cereals. Processing these foodstuffs with hemicellulases converts them to a more edible form, thereby improving the energy value of the product, and reduces solution viscosity. Hemicellulases have thus been used to clarify fruit juices, to reduce the viscosity of slurries or purees, to liquefy certain cell wall solids and to modify taste. Similarly, hemicellulases have also been employed to mitigate problems associated with the presence of hemicellulose and other minor polysaccharides in pulps and in unprocessed cotton. By the same token, hemicellulose is a problem when it is present in sewage and industrial waste-water treatment, and in fracturing fluids used in the conditioning of oil-bearing well formations.

Some processes involved in commercial applications utilizing hemicellulose are characterized by conditions of high temperatures and high alkalinity. Hemicellulases in general, and mannanases heretofore described in particular, exhibit substantial activity at a pH range of 3–8 and temperatures below 60° C. These enzymes therefore cannot be used to process hemicellulose cost effectively in applications where these conditions are exceeded.

Nonspecific oxidizing chemicals have been employed to degrade hemicellulose in many commercial oil well fracturing solutions in the exceeded conditions. Incomplete degradation of the hemicellulose is effected, however, at all pHs and temperatures. This can prove to be inefficient, at best, thereby increasing processing costs and resulting in marginal usefulness. For example, partial degradation of mannan-based hydraulic gels, either by chemical oxidizers or by enzymes, leaves a residue that cannot be adsorbed into the surrounding formation. This may lead to a situation whereby the residue can coat fracture surfaces, thereby impeding oil exiting the formation. Accordingly, there is a need for a hemicellulase capable of retaining a substantial portion of its activity in conditions of high alkalinity and at temperatures exceeding 60° C. Such an enzyme would permit complete and efficient degradation of hemicellulose and modified hemicellulose under the conditions that prevail in most of the commercial processes involving hemicellulose-based hydraulic gel.

SUMMARY OF THE INVENTION

It is therefore an object of the present invention to provide a hemicellulase that displays substantial biological activity under conditions of high temperature and high alkalinity.

It is another object of the present invention to provide a method of isolating a microorganism capable of producing a heat and alkaline-resistant hemicellulase, as well as to provide a microbial culture consisting essentially of cells that produce the foregoing hemicellulase.

It is yet another object of the present invention to provide a method of producing commercially useful quantities of the foregoing hemicellulase.

A further object of the present invention is to provide a means for degrading mannan-based hemicelluloses under conditions of high alkalinity and elevated temperature such as are commonly found, for example, in the subterranean conditioning of oil fields, in the processing of some paper pulps and certain food materials, and in sewage and industrial waste-water treatment.

In accomplishing the foregoing objects, there has been provided, in accordance with one aspect of the present invention, an enzyme in substantially pure form that catalyzes the degradation of hemicellulose and that has a pH profile for its heiceullose-catalyzing activity that ranges from about pH 4.5 to about pH 11. In certain preferred embodiments, the pH profile of the enzyme peaks between about pH 7 and about pH 9, and the enzyme catalyzes the degradation of a mannan-containing hemicellulose. In another preferred embodiment the enzyme is one that can catalyze the degradation of hemicellulose even when both pH and temperature are elevated into the range of 8–11 and to at least 60° C., respectively.

In accordance with another aspect of the invention, a microbial culture is provided that consists essentially of cells that produce an enzyme as described above. In a preferred embodiment, the microbial culture consists essentially of Gram-positive bacteria of a Bacillus species, such as *B. circulans*.

In accordance with other aspects of the present invention, an isolated polynucleotide is provided that codes for an enzyme that catalyzes the degradation of hemicellulose, said enzyme having a pH profile for its activity in catalyzing the degradation of hemicellulsoe that ranges from about pH 4.5 to about pH 11. Also provided are (i) a vector comprising a nucleotide sequence coding for such an enzyme and (ii) a host cell transformed with such a vector in order that the host cell expresses the enzyme.

In accordance with yet another aspect of the invention, a method of producing commercially useful quantities of the foregoing hemicellulase is provided, comprising the steps of:

(a) growing the microbial culture in a suitable broth medium;

(b) adding a mannan-containing hemicellulose to the broth culture during the growth phase or the stationary phase of the microorganism;

(c) obtaining a culture supernatant from the broth culture, the supernatant comprising a predetermined concentration range of the hemicellulase;

(d) removing the hemicellulase by ultrafiltration;

(e) precipitating the hemicellulase with a precipitating agent selected from the group consisting of acetone and methanol; and (f) recovering the hemicellulase.

In accordance with a further aspect of the invention, a method is provided for conditioning subterranean oil wells comprising the steps of:

(a) preparing a suspension comprised of water, a hydraulic gelling agent and a proppant, the proppant having an indicated acceptable mesh size;

(b) pumping an adequate amount of the suspension into an oil well under high pressure causing a fracture to occur in subterranean geologic formations adjacent to the well such that the suspension is deposited in the fracture;

(c) pumping an adequate amount of the foregoing hemicellulase with the suspension into the fracture to effect controlled degradation of the hydraulic gelling agent.

Other objects, features and advantages of the present invention will become apparent from the following detailed description. It should be understood, however, that the detailed description and the specific examples, while indicating preferred embodiments of the invention, are given by way of illustration only since various changes and modifications within the spirit and scope of the invention will become apparent to those skilled in the art from this detailed description.

BRIEF DESCRIPTION OF THE DRAWINGS

In drawings which illustrate embodiments of the invention.

DETAILED DESCRIPTION OF THE PREFERRED EMBODIMENTS

Figure 1:
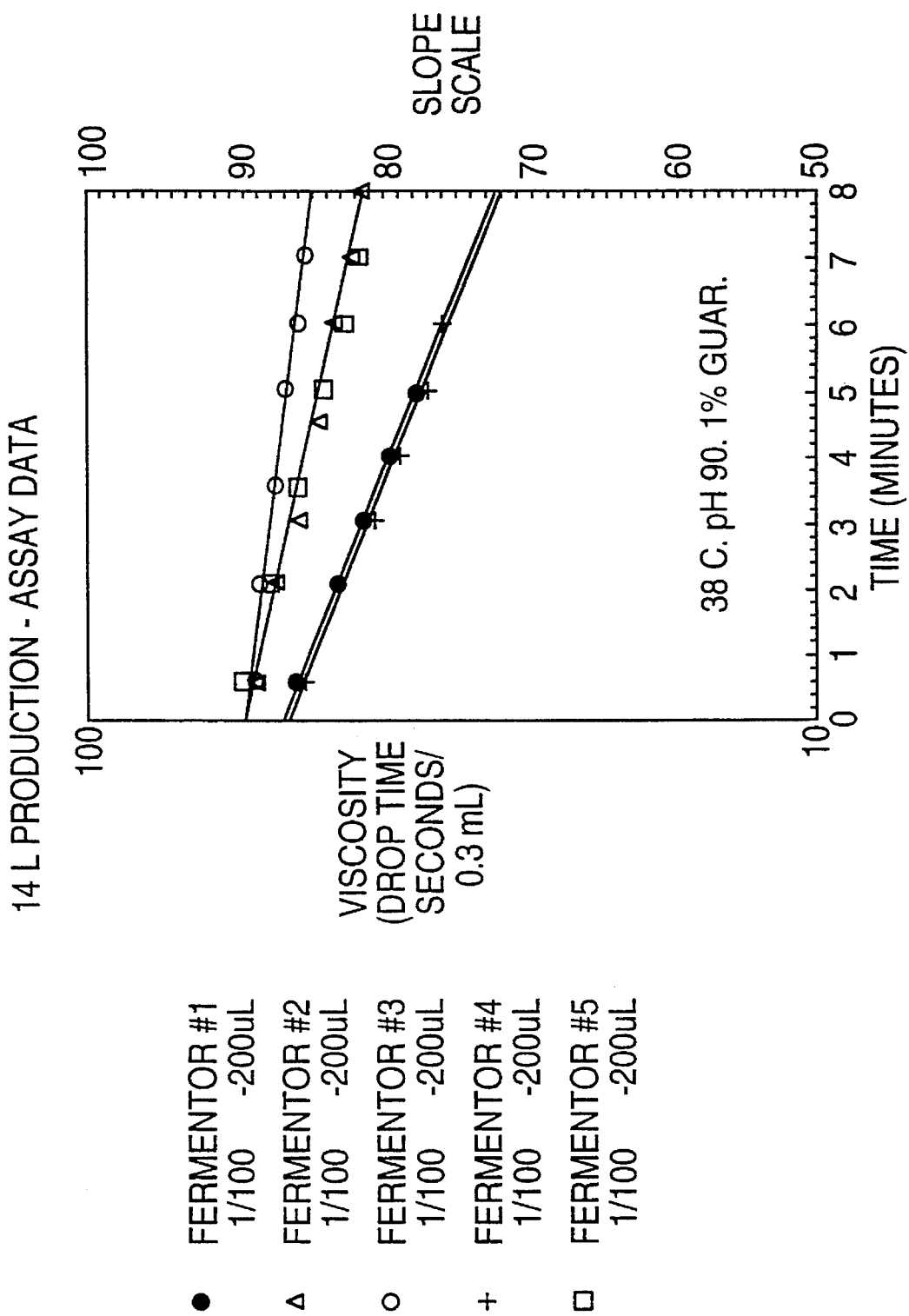
FIG. 1 presents representative data showing the reduction in viscosity in relation to the amount of time that enzyme dilutions from 14 liter fermentations were incubated with the guar solution.

It has been discovered that a hemicellulase capable of catalyzing the degradation of mannan-containing hemicellulose under conditions characterized both by high alkalinity and by high temperature can be produced using microorganisms that synthesize the enzyme. Microorganisms possessing the ability to produce a hemicellulase within the present invention can be isolated by conventional methods from the soil, where they comprise a reproducible, finite subsection of indigenous microflora. Hemicellulase-producing microorganisms can also be produced by transforming another microorganism of choice, such as *B. subtilis* or *B. brevis*. Transformation may proceed with hemicellulase-encoding DNA obtained, via standard recombinant DNA techniques, from such indigenous soil microflora.

In cultures consisting essentially of microorganisms that produce a hemicellulase within the present invention, commercially significant quantities of the enzyme can be obtained by isolation techniques that are well known in the art. In this description, a "culture consisting essentially of a specified type of microorganism," such as a hemicellulase-producing microorganism, is a culture that is comprised primarily of microbes of that type, to the extent that the salient functional property or properties of the culture are determined by those microbes. But other types of microorganisms may be present, for example, in a culture consisting essentially of a hemicellulase-producing microorganism, so long as the other types do not interfere significantly with hemicellulase production by the culture.

Microorganisms producing a hemicellulase with the foregoing properties can be isolated, pursuant to the present invention, from soil samples collected from diverse geographical areas. The soil samples are collected primarily from the top two inches of soil and cultured in selective enrichment media.

Techniques for selectively isolating microorganisms with certain desired characteristics are well known in the art. Microorganisms can be selected for the capacity to produce a particular enzyme by exposing samples potentially containing such microorganisms to conditions wherein replication and growth are dependent upon the capacity to produce the desired enzyme. One widely used method of selection is exposing a sample containing a large, diverse microbial population to a medium consisting of a single carbon source. See 160 METHODS IN ENZYMOLOGY 180-86 (1988). Only those microorganisms capable of producing enzymes that can degrade the carbon source will be recovered by this method. Selective culturing techniques of this sort effectively separate microorganisms producing the desired enzyme from the myriad of other microorganisms comprising the normal flora of the habitat sampled.

In a preferred embodiment of the present invention, aliquots of soil samples are inoculated into an alkaline culture medium, wherein hemicellulose serves as the sole carbon source. Dilutions of the sub-cultures grown in the same medium are plated out onto a solid medium which also contains hemicellulose as the sole carbon source. Morphologically distinct colonies are isolated and then screened for hemicellulase activity. In a particularly preferred embodiment of this invention, a selective enrichment broth at a pH range of 9-9.5, wherein purified guar gum is the sole carbon source is inoculated with a sample of soil, incubated at 37° C. and aerobically agitated.

After incubation, further dilutions of the initial culture are made using the selective enrichment broth. After several passages, a dilution series of the most dilute broth culture is made in normal saline and plated out on a solid medium which contains guar as the sole carbon source. After incubation at 34° C. for 5-7 days, morphologically distinct colonies are isolated from the solid medium and screened for hemicellulase activity.

The initial selection for microorganisms which utilize hemicellulose as a sole carbon source at an elevated pH results in the recovery of a finite fraction of all soil microorganisms. Typically, about 40% of the isolates are characterized by an ability to produce a hemicellulase within the present invention. A particularly preferred subgroup of this fraction includes species of the Gram-positive genus Bacillus.

Exemplary of this preferred subgroup is a strain of *B. circulans*, designated CMG1240, the general properties of which are summarized in Table 1. Strain CMG1240 was deposited on May 9, 1990, in accordance with the Budapest Treaty, at the American Type Culture Collection 12301 Parklawn Drive, (Rockville, Md. 20852) under accession No. 55045. All restrictions imposed by the depositor on the availability to the public of the deposited material will be irrevocably removed upon the granting of the patent. This deposit has been made before pendency of the application for patent and for a term of at least thirty (30) years and at least five (5) years after the most recent request for the furnishing of a sample of the deposit was received by the depository and after the enforceable life of the patent. The key characteristic of strain CMG1240, as for any microbial strain of the preferred subgroup, is its ability to produce in culture medium a hemicellulase according to the present invention.

TABLE I a. Morphology
   (1) bacillus shape; (0.8×1.7–2.3) μm
   (2) occurs predominately in singles and pairs
   (3) capable of forming endospores
   (4) Gram-positive (also appears Gram-variable or Gram-negative)
b. Growth Conditions
   Tryptic soy agar plate culture: colonies are irregular, convex, smooth, undulate, butyrous, opaque and 2 mm in diameter (72 hours, 37° C.).
c. Biochemical Properties:
   (1) Aerobic
   (2) Catalase positive
   (3) Oxidase negative
   (4) Non-motile
   (5) Growth temperature: 30°–50° C., maximum growth rate occurring at 41° C.
   (6) Growth pH (cultured at 34° C. at 350 rpm for 10 hours in a basal glucose-mineral salts medium): 7.0–8.5, maximum growth rate occurring at pH 7.5
   (7) Casein and gelatin decomposition: negative
   (8) Starch hydrolysis: positive
   (9) Growth in 1–5% NaCl: positive
   (10) Carbon sources utilized include: D-glucose, D-galactose, D-fructose, D-xylose, lactose, maltose, sucrose, alpha-cyclodextrin, dextrin, glycogen, N-acetyl-glucosamine, L-arabinose, cellobiose, gentiobiose, lactulose, mannitol, D-mannose, D-melibiose, D-trehalose, turanose, α-ketobutyric acid, uridine, and m-inositol.
   (11) Hydrogen sulfide production: negative
   (12) Indole production: negative
   (13) Utilization of citrate: negative
   (14) Urease: negative
   (15) Voges-Proskauer: negative
   (16) Phenylalanine deaminase: negative
   (17) Lysine decarboxylase: negative
   (18) Ornithine decarboxylase: negative
   (19) Arginine dehydrolase: negative Conventional methods for measuring cellulase/hemicellulase activities are described, for example, in 160 METHODS IN ENZYMOLOGY 180–86 & 368–76 (1988). These methods generally entail exposing a predetermined amount of a substrate to a predetermined amount of a enzyme preparation, crude or purified. The rate of conversion of the substrate to the desired end product is measured under specified conditions of pH and temperature. Crude enzyme preparations can be produced by culturing microorganisms in a suitable medium and then concentrating the enzyme that accumulates in the broth surrounding the cells using conventional means such as precipitation or ultrafiltration. The resulting enzyme preparations can be assayed for specific activity by methods known to the art, including those that are keyed, respectively, to weight loss of insoluble substrates, changes in turbidity of polysaccharide suspensions, an increase in reducing end groups, a decrease in the viscosity of polysaccharides such as beta-mannans, colorimetric determinations, measurements of clearance zones in polysaccharide-agar, or polarography.

In accordance with the present invention, soil isolates are screened for hemicellulase production by culturing isolated colonies of the microorganisms in a hemicellulose-containing broth medium. After incubation, the broth medium is centrifuged and the resulting supernatant is filtered to remove cells and to produce a crude preparation of hemicellulase. The enzyme is added to alkaline, viscous preparations of a preferred hemicellulose and the degree of liquefaction of the substrate over time is measured.

In a preferred embodiment of the present invention, soil isolates are cultured in a broth medium, wherein a mannan-containing hemicellulose is the sole carbon source. After incubation, the broth medium is centrifuged and the resulting supernatant is filtered. The resulting crude enzyme preparation is added to a highly viscous preparation of a mannan-containing hemicellulose at a pH in the range of 8–11. The relative activity of the enzyme is determined by the amount of time required to liquefy the hemicellulose.

In a particularly preferred embodiment of the present invention, soil isolates are cultured in a selective enrichment medium, wherein guar is the sole carbon source. After incubation, the culture is centrifuged and the resulting supernatant filtered to recover crude enzyme. The crude enzyme is then introduced into tubes containing a cross-linked guar preparation, with metal ions added to enhance the viscosity of the preparation, at a pH in the range of 9–9.5. After incubation for at least one hour at 39°–40° C., enzyme activity is measured by determining the viscosity of a enzyme/guar solution using conventional viscosimetric procedures. See, e.g., *Biochim. Biophys. Acta* 139: 238 & 248 (1967); *Eur. J. Biochem.* 51: 207 (1975).

A hemicellulase obtained as described above will generally display an activity characterized by a pH profile—the curve defined by the relationshop between a given enzymatic activity and pH—that ranges over some 6.5 pH units, between minima at about pH 4.5 and about pH 11, respectively. A pH profile of this sort is highly distinctive when compared, for example, to corresponding profiles for known Bacillus mannanases, which are virtually inactive at above about pH 8. See Araujo & Ward, *J. App. Bacteriol.*, 68: 253–61 (1990).

A hemicellulase used in the present invention preferably has a pH profile with a peak (i.e., the portion of the profile where activity is greatest) that is in a range from about pH 9 to above about pH 7. It is also preferred that the enzyme display significant biological activity under conditions characterized both by high alkalinity and by elevated temperatures. Such a suitable enzyme would be active, for example, when pH is in the range of 8–11 and the temperature is 60° C. or higher.

A hemicellulase particularly preferred for use according to the present invention is an endo-β-D-mannanase having the following properties:

(1) Activity: A preferred enzyme acts on hemicellulosic materials containing mannan carbohydrates like galactomannan, glucomannan and mannan. Activity in this context can be measured in the following way. An aqueous suspension containing 1.0% guar is used as a substrate, and 2 mL of 2M glycine is added to 16.0 mL of the substrate. The mixture is mixed thoroughly and then preheated to 38° C. Enzyme is added to the substrate, mixed well and then the viscosity of the enzyme/guar solution is measured using a simple approach, as by timing the charging and discharging of a pipette with stopwatch, or more complex devices like Brookfield or Fann viscometers. A standard curve is prepared using a commercially available hemicellulase enzyme with known activity such as Miles B1500. Grams or units of the commercially available hemicellulase are plotted against the time required to change viscosity and the new hemicellulase is compared to that of the commercial product.

(2) Substrate specificity: The enzyme degrades relatively simple carbohydrate polymers like guar gum, which is a polymer of D-mannose linked β-1,4 with D-galactose, and locust bean gum, as well as more complex, mannan-containing carbohydrates, for example, from soybean and alfalfa. Other suitable substrates will include mannan-containing coconut residue, carob bean gum, cassava, copra, and chemically-modified forms of guar.

(3) Optimum pH: The optimum pH of the enzyme is about 7.0 or slightly above, e.g., in the range 7.1 to 7.5. The enzyme is stable in a pH range of about 4.5 to 11 (see FIG. 4).

Figure 2:
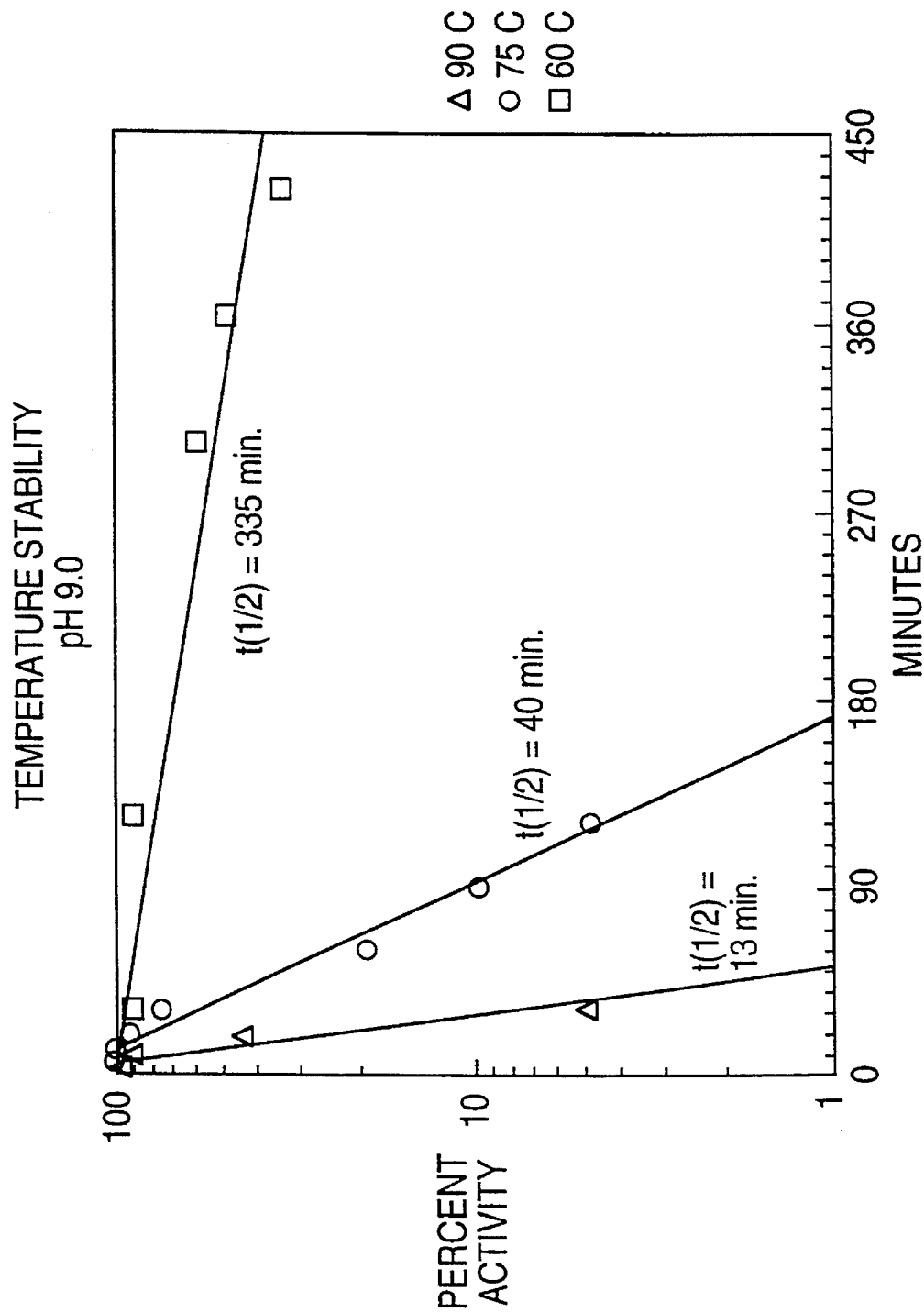
FIG. 2 is a graph which plots the activity of a hemicellulase within the present invention versus time (pH 90) at 60°, 75° and 90° C., respectively.

(4) Optimum temperature: The optimum temperature for enzyme activity is 40° C., but enzyme activity is observed at temperatures ranging from 20° to 90° C. As shown in FIG. 2, the enzyme exhibits significant activity at temperatures ranging from 60° C. to 90° C.

(5) Deactivation by Temperature and pH: At pH 9.0 the enzyme retains 50% of its maximum activity after 5.5 hours at 60° C., after 45 minutes at 75° C., and after 15 minutes at 90° C. (see FIG. 2).

(6) Molecular Weight: After purification to homogeneity, the enzyme has a molecular weight of about 32,000 as determined by SDS-polyacrylamide gel electrophoresis. To obtain a crude enzyme preparation from culture broth, cells and debris are first removed with a 0.1-micron filter. The enzyme is then concentrated with a membrane having a 10,000 molecular weight cut-off. Once the enzyme becomes quite concentrated, however, a good proportion of the enzyme is able to pass through the membrane. The enzyme in this final permeate can be concentrated using a membrance with a 5,000 molecular weight cut-off, or can be precipitated with three volumes of acetone. After the precipitate is centrifuged, the supernatant is siphoned off and the pellet resuspended in 50 mM phosphate buffer. This concentrate is dialyzed versus 10 mM phosphate buffer (pH 7.0) and then applied to a DEAE-Sephacel column. The enzyme is eluted with a solution gradient of sodium chloride of increasing ionic strength ranging from 0–1.25M in 50 mM phosphate buffer (pH 7.0). Fractions are collected and tested for enzyme activity. The fractions exhibiting maximum activity are pooled and examined using SDS-polyacrylamide gel electrophoresis and compared to protein molecular weight standards.

Pursuant to the present invention, commercially useful quantities of hemicellulase can be produced by culturing the foregoing hemicellulase-producing microorganisms using conventional fermentation techniques. In this context, "fermentation" is used broadly to refer to any controlled microbial action by which useful products are obtained from the substrate(s) of that action. In accordance with the present invention, fermentation can be carried out in a stirred-tank reactor. This type of reactor is essentially a closed cylindrical tank containing agitators, baffles, heat exchange coils, and automatic controls for temperature, air flow, pressure, pH and foaming. A fermenter of this sort would be charged with essential nutrients and a hemicellulase inducer. After sterilization, the reactor is inoculated with a culture consisting essentially of microorganisms that have been selected for their capacity to produce hemicellulase as described above.

Continuous culture can increase fermenter productivity by eliminating the downtime of batch cultures. But it is sometimes difficult to maintain sterility in large scale continuous cultures. Accordingly, batch fermentations which utilize the bacteria of the present invention are preferred.

In a preferred embodiment of this invention, a Gram-positive Bacillus strain like *B. circulans* CMG1240 is utilized to produce commercially useful quantities of the enzyme. A fermenter charged with a medium consisting of industrial-grade nutrients, glycerol (carbon source) and a mannan-containing hemicellulose, such as guar gum, is inoculated with a culture consisting essentially of a Gram-positive Bacillus strain as described above. The fermenter is maintained at about 35° C. (500–1,000 rpm agitation with an air flow between 0.4 and 1.6 vvm) for about 12 hours. The hemicellulose, such as guar, is added to the fermenter during the growth phase to further induce enzyme production. The fermentation is harvested after about 1 to 7.5 hours, and then enzyme activity is measured by viscometric means.

Enzyme activity of the fermentation product is assayed by centrifuging aliquots of the fermentation broth and testing the resultant supernatant. Aliquots of the supernatant (or dilutions thereof) are added to a guar solution and any reduction in the viscosity of the enzyme/guar solution is measured routinely by recording the time required for a constant bore pipette to discharge a predetermined volume, as described above in (1) of the preferred hemicellulase properties.

The enzyme is recovered from the fermentation broth by filtration through a 0.5-micron filter to remove cells followed by ultrafiltration using a 5,000 or 10,000 molecular weight cut-off ultrafiltration membrane. The concentrate is combined with three volumes of acetone at about 4° C. to precipitate the enzyme. The precipitate is allowed to settle for approximately 24 hours before the supernatant is siphoned off. The precipitate is then centrifuged at about 4° C. and the resultant pellet resuspended in phosphate buffer.

The preparation thus obtained represents a substantially pure form of the inventive enzyme, that is, a preparation in which virtually no other enzymatic activity is represented other than the hemicellulase activity described above. From such a preparation, other formulations can be made that consist essentially of the inventive enzyme; in other words, the enzyme may be present with other components of the formulation, including other enzymes, that do not unduly hinder the desired hemicellulase activity. For example, a hemicellulase of the present invention may be included in a pulp-treating formulation which also includes lignin-degrading enzymes.

In an alternative method for producing a hemicellulase within the present invention, DNA encoding hemicellulase could be isolated and used, via known procedures, to transform a suitable host organism such that the enzyme is produced by the recombinant host in commercially useful amounts. Hemicellulase-encoding DNA could be isolated by screening nucleic acid libraries generated from microorganisms expressing a hemicellulase according to the present invention. See, e.g., Ausubel et al., CURRENT PROTOCOLS IN MOLECULAR BIOLOGY at 5 & 6, John Wiley and Sons, New York (1987, 1990) (hereafter "Ausubel"). Such libraries would be screened by means of oligonucleotide probes that are complementary to a polynucleotide encoding, for example, a portion of the N-terminus of a hemicellulase within the present invention. Illustrative of such an N-terminal portion is the amino acid sequence Ala-Ser-Gly-Phe-Tyr-Val-Xxx-Gly-Thr-Ile-Leu-Xxx-Asp-Ser-Thr-Gly-Asn-Pro-Phe-Lys-Ile-Xxx-Gly-Xxx-Asn ["Xxx" denotes an indeterminant amino acid], as discussed in Example 12 below. See Ausubel at 6.

Alternatively, other portions including or adjacent to the endogenous coding sequence of a hemicellulase according to the present invention can be used, when isolated using a probe as a template for generating other probes useful for isolating a hemicellulase-encoding polynucleotide according to the present invention, e.g., based on the N-terminal sequence described above. Such a probe could be used in a known manner to screen a genomic or cDNA library as described above, see Ausubel, loc. cit., or to synthesize polymerase chain reaction (PCR) probes for use in amplifying a cDNA generated from an isolated RNA which codes for a hemicellulase of the present invention. Such a cDNA could then be cloned into a suitable expression vector and employed to transform a host organism. See Ausubel at §15.4.

A suitable polynucleotide in this regard would preferably comprise a nucleotide sequence, corresponding to the desired amino-acid sequence, that is optimized for the host of choice, as described below, with regard to codon usage, the initiation of translation, the most appropriate glycosylation pattern (if applicable), and the expression of recoverable amounts of a commercially useful hemicellulase within the present invention. Also, a vector selected for transforming the chosen host organism with such a polynucleotide molecule should allow for efficient maintenance and transcription of the sequence encoding the polypeptide. Such a vector is readily available or derivable from commercial sources, and is suited to a particular host cell employed for expressing a hemicellulase according to the present invention. For vectors exemplary of those suitably used to the present invention, see Ausubel at §§2–4.

Host cells suitable for expressing a hemicellulase according to the present invention would include prokaryotic or eukaryotic cells, for example, bacterial, algal, yeast, insect, mammalian and human cells. Thus, among host cells suitable for the present invention would be microorganisms of the genera Aeromonas, Aspergillus, Bacillis, Echerichia, Kluyveromyces, Pichia, Rhodococcus, Saccharomyces and Streptomyces. More specifically illustrative of the suitable host microorganisms would be the bacteria *E. coli*, *B. subtilis*, *B. brevis* (*J. Bacteriol.* 172: 1312–20) and *B. circulans*, as well as the yeast *S. cerevisiae* strain X2181-1B, with genotype α trp1 gal1 ade1 his2 (available from the Yeast Genetic Stock Center, Berkeley, Calif.); strain ATCC 52683, with genotype α his2 ade1 trp1 met14 ura 3 (available from the American Type Culture Collection, Rockville, Md.); and strain ATCC 46183, with genotype α his1 trp1 (also available from the American Type Culture Collection). Host cells comprising a polynucleotide encoding a hemicellulase according to the present invention can be grown under conditions that provide expression of a hemicellulase of the present invention in recoverable or commercially useful amounts. See, e.g., Ausubel at §§ 1 & 13.

A microorganism that produces a hemicellulase according to the present invention can be utilized to degrade a gelling agent used to fracture an oil well. More specifically, it is well known in the art to use mixtures of hydraulic gelling agents such as guar, proppants such as sand, glass bead and stones; and water in fracturing oil wells. Pumping such a mixture into a well at high pressure causes expansion of any natural fracture in a subterranean geologic formation adjacent to the well, resulting in a subsequent depositing of the mixture throughout the formation. But in order to obtain oil from the treated formation, the hydraulic gelling agent, preferably guar-based, must be removed.

Temperatures at the fracture site can range from ambient to 200° C. and the ground water is generally alkaline with a pH range of 4.0 to 12.0 with a large percentage between pH 9.0 to 12.0. Pursuant to the present invention, a thermostable, alkaline-resistant hemicellulase can be utilized to degrade a guar-based hydraulic gelling agent deposited in such a fracture. In a preferred embodiment, an effective amount of hemicellulase according to the present invention is added to a mixture of cross-linked guar and sand at the well head, immediately prior to the mixture being pumped down the well into the formation. Pressure is maintained on the well for 1–48 hours. In a controlled manner, the hemicellulase completely degrades the guar solution into small-molecule material of low viscosity, permitting extraction of oil from the newly fractured rock formation.

The present invention is further described below by reference to the following illustrative examples, in which the following media were used:

| Selective Enrichment Broth (amount/liter) | |
|---|---|
| 10.0 g | Guar Gum |
| 5.0 g | $(NH_4)_2SO_4$ |
| | pH 9.5 |

| Selective Enrichment Agar (amount/liter) | |
|---|---|
| 2.0 g | Guar Gum |
| 1.0 g | $Na_2HPO_4$ |
| 3.0 g | $(NH_4)_2SO_4$ |
| 0.2 g | NaCl |
| 0.2 g | $MgSO4.7H_2O$ |
| 50.0 mg | $CaCl2.2H_2O$ |
| 1.0 mL | Trace Elements Solution I (see below) |
| 15.0 g | Agar Noble |
| 50.0 mM | Tris Buffer (pH 9.0) |
| 1.0 mL | Vitamin Solution (see below) |

| Trace Elements Solution I (amount/liter) | |
|---|---|
| 100.0 mg | EDTA |
| 230.0 mg | $ZnSO_4.7H_2O$ |
| 180.0 mg | $MnSO_4.H_2O$ |
| 60.0 mg | $H_3BO_3$ |
| 100.0 mg | $CuSO_4.5H_2O$ |
| 40.0 mg | $Na_2MoO_4.2H_2O$ |
| 40.0 mg | $CoCl_2.6H_2O$ |
| 70.0 mg | KI |
| 40.0 mg | $FeSO_4.7H_2O$ |
| 0.4 mg | $NiCl.6H_2O$ |
| 8.0 μL | $0.1\ M\ H_2SO_4$ |

| Vitamin Solution I (amount/liter) | |
|---|---|
| 1.0 g | Vitamin B12 |
| 1.0 g | Riboflavin, B2 |
| 1.0 g | Pyridoxine, B6 |
| 1.0 g | D-biotin |
| 1.0 g | Thiamine Hydrochloride |
| 1.0 g | Nicotinic Acid |
| 1.0 g | D-Ca-Pantothenic acid |

| Seed Broth (amount/liter) | |
|---|---|
| 7.5 g | Glycerol |
| 10.0 g | Yeast Extract |
| 2.5 g | Corn Steep Liquor |
| 1.0 g | $KH_2PO_4$ |
| 2.0 g | $(NH_4)_2SO_4$ |
| 0.5 g | $MgSO_4.7H_2O$ |
| 1.0 mL | Trace Elements Solution II (see below) |
| | pH 7.0–7.5 |

| Fermentation Broth (amount/liter) | |
|---|---|
| 20.0 g | Glycerol |
| 20.0 g | Yeast Extract |
| 5.0 g | Corn Steep Liquor |
| 2.0 g | $KH_2PO_4$ |
| 4.0 g | $(NH_4)SO_4$ |
| 1.0 g | $MgSO_4.7H_2O$ |
| 2.0 mL | Trace Elements Solution II |
| | pH 8.5 |

| Trace Elements Solution II (amount/liter) | |
|---|---|
| 20.0 g | $FeSO_4.7H_2O$ |
| 20.0 g | $FeCl_3.6H_2O$ |

| | |
|---|---|
| 0.5 g | MnSO$_4$.H$_2$O |
| 50.0 mg | CoSO$_4$.7H$_2$O |
| 10.0 mg | CuSO$_4$.5H$_2$O |
| 20.0 g | CaCl$_2$.H$_2$O |
| 50.0 mg | H$_3$Bo$_3$ |
| 100.0 g | ZnSO$_4$.7H$_2$O |
| 100.0 9 | Na$_2$MoO$_4$.2H$_2$O |

EXAMPLE 1

Isolation of Hemicellulase-producing Microorganisms from Soil

Soil samples collected from both a tropical rain-forest and a temperate garden were added to selective enrichment broth in a 10% w/v concentration. The cultures were shaken in baffled Erlenmeyer shake flasks at 37° C. for 4 days. Four dilutions [1:10, 1:20, 1:800 and 1:50,000] of the initial cultures were made with fresh selective enrichment broth and incubated at 37° C. for 4 days. The 1:50,000 dilution was used to prepare a dilution series ($10^{-1}$ to $10^{-8}$) in 0.85% NaCl which were plated out on selective enrichment agar and incubated at 34° C. for 5–7 days. Following incubation, isolated colonies were selected from the plated cultures and streaked for purity three successive times on a suitable agar medium. Nine isolates from soil collected from a tropical rain-forest and 24 isolates from soil collected from a temperate garden were selected as a result of this screening process.

EXAMPLE 2

Screening of Soil Isolates for Hemicellulase Activity

Each purified isolate from the tropical rain-forest soil was transferred to a shake flask containing selective enrichment broth and shaken for 48–72 hrs at 34° C. After incubation, the culture was centrifuged for 20–30 minutes at 10,000 rpm (4° C.). The resultant supernatant was filtered sequentially through a 0.8- and a 0.45-micron filter to recover crude enzyme free of microbial cells. Each purified isolate from the temperate garden soil was transferred to tubes containing selective enrichment broth and shaken 12–48 hours at 34° C. After incubation, the cultures were centrifuged and filtered as described above. The crude enzyme solution was added to tubes containing 5 mL of a cross-linked guar preparation (5.0 g guar, 2.0 g (NH$_4$)$_2$SO$_4$ and 0.6 g sodium tetraborate per 400 mL water, pH 9.5) and incubated for at least 1 hour in a water bath at 39°–40° C. To measure enzyme activity, a constant bore, 1-mL pipette was charged with 1.0 mL of the mixture and allowed to discharge 0.9 mL. A stopwatch was used to measure the time required for this discharge to occur ("drop time"). A drop time of less than two seconds indicated measurable amounts of hemicellulase activity. Twelve of the twenty-four isolates recovered from temperate garden soil, and four of the nine isolates recovered from tropical rain-forest soil produced measurable amounts of hemicellulase.

EXAMPLE 3

Production of Commercially Useful Quantities of Hemicellulase

A single, isolated colony of *B. circulans* (CMG1240) was inoculated into a 500 mL Erlenmeyer baffled shake (pre-seed) flask containing 50 mL of brain heart infusion broth. The inoculated flask was shaken (300 rpm) while incubating for 12–16 hours at 35° C. After incubation, the entire volume of the pre-seed flask was aseptically transferred to a 4 L Erlenmeyer baffled shake-flask (seed) containing one liter of seed medium. The seed-flask was incubated with shaking for 12–16 hours at 35° C. The entire volume of the seed flask was aseptically transferred to a 14-liter fermenter containing 9.0 liters of fermentation broth. The fermenter was maintained at 40° C., >20% dissolved oxygen and 500–1000 rpm. Guar gum was added to make a final concentration of 0.05% to the fermenter 2 or 3 times during the growth phase and once (0.5%) during the stationary phase to induce enzyme production. After 1–7.5 hours, the fermentation was terminated and enzyme activity assayed according to the procedure of Example 5. Assay data are shown in FIG. 1.

EXAMPLE 4

Measurement of Hemicellulase Activity to Determine Optimal Culture Conditions for Hemicellulase Production Twenty-milliliter aliquots of 1% guar in water, mixed for 3 hours to obtain the maximum viscosity, and 2 mL aliquots of 2M glycine-NaOH buffer (pH 9.0) were added to a glass-jacketed reactor maintained at 40° C. by means of a circulating water bath. Aliquots of the fermentation product were centrifuged in a Microfuge for 5 minutes and the resultant supernatant was used to test for enzyme activity. A 100–200 μL sample of the supernatant was added to the reactor. Enzyme activity was measured as described in Example 5. Sample enzyme activity was calculated from a standard curve prepared by plotting the log of the drop time (seconds) of dilution of a standard hemicellulase (Miles B-1500) versus incubation time (minutes). The slope (on a linear scale) of the log plot was calculated and replotted versus grams or "chamber units" of hemicellulase.

EXAMPLE b 5

Assay for Hemicellulase Activity Suitable for Testing Standards and Purified Enzyme Preparations In a procedure suitable for screening enzyme activity of standard hemicellulase or purified enzyme preparations, approximately 16.0 mL of a guar preparation, comprising 1% guar gum in water, and 2.0 mL of 2M glycine (adjusted to pH 9.0 with NaOH), were added to a 100 mL glass jacketed reactor maintained at 38° C. by means of a circulating water bath. The solution was mixed thoroughly by a magnetic stirrer after reaching temperature. Viscosity at time zero was determined by measuring the time required for the solution to drop from the 1.0 mL mark to the 0.7 mL mark in a constant bore, 1 mL pipette. The initial drop time of the guar solution without enzyme added was 75 to 90 seconds. After enzyme addition (200–500 μL) to the reactor, the guar/enzyme solution was allowed to incubate. A time-zero measurement of the solution was immediately determined. Drop time measurements were performed until either 5 measurements had been made or until the drop time was less than 30 seconds. A standard curve was prepared by plotting the log of the drop time versus the time of incubation using different standard enzyme dilutions.

EXAMPLE 6

Recovery of Hemicellulase from Fermentation

The procedure described in Example 3 was used in the production of useful quantities of hemicellulase in each of six 14-liter fermentations. After the fermentation was terminated, cells were removed from 60 L of culture broth by ultrafiltration with a 0.1 micron filter. Then, the enzyme was concentrated to a volume of approximately 3.5 L with a 10,000 molecular weight cut-off ultrafiltration membrane. The concentrate was combined with three volumes of acetone at 4° C. to precipitate the hemicellulase. The precipitate was collected by allowing it to settle for 24 hours and then siphoning off the supernatant. The precipitate was then centrifuged at 6000 rpm for 10 minutes at 4° C. The resulting pellet was immediately resuspended in 170mL of 50 mM potassium phosphate buffer (pH 7.0) to a final volume of 300 mL. The enzyme activity was determined according to the method of Example 5. The recovered hemicellulase had $9.45 \times 10^6$ chamber units/liter, which was equivalent to 6.3= kg/L of standard commercial hemicellulase (assayed at pH 9.0) or 1.89 kg/L total of standard hemicellulase formulation.

EXAMPLE 7

Alternate Process for Recovering Hemicellulase

Hemicellulase was recovered by the method described in Example 6, wherein methanol was used alternatively to precipitate hemicellulase. The supernatant was siphoned off and the precipitate centrifuged as described above. The paste-like precipitate was then blended with 10 volumes (w/w) of lactose and dried under vacuum at temperatures up to 40° C.

EXAMPLE 8

Purification of Hemicellulase

To produce a more purified product, two precipitation steps were used to obtain refined enzyme. A concentrate from ultrafiltration was prepared according to the method described in Example 6. The concentrate contained $6.39 \times 10^6$ units/liter, with a specific activity of $1.11 \times 10^3$ units/mg. Equal volumes (2.2 liters) of the concentrate and acetone were mixed to make a 50% (v/v) solution, and the resultant precipitate was then allowed to settle for 18 hours at 10° C. After the supernatant was collected, an additional volume of acetone was added to make the solution 75% (v/v). The resultant precipitate was allowed to settle for 24 hours at 10° C., after which the supernatant was first removed by siphoning and finally by centrifugation at 5000 rpm. The precipitate was then dissolved in 222 mL of 50 mM phosphate buffer (pH 7.0). Activity was determined to be $5.71 \times 10^7$ units/liter, with a specific activity of $6.17 \times 10^3$ units/mg. This purification step resulted in a recovery of 90% of the total activity with only 20% of the protein, causing a 5.56 fold increase in the specific activity.

EXAMPLE 9

Alternative Hemicellulase Purification Process

An alternative purification process was employed to avoid the precipitation step of Example 8. The hemicellulase was concentrated to the desired concentration by ultrafiltration as described in Example 6. A liquid formulation of the concentrate was then prepared by adding stabilizing and preservative agents such as ethylene glycol, or alternatively, glycerol, methanol, ethanol, sorbitol, sodium benzoate, sodium citrate, methylparaben, sodium ascorbate or an equivalent.

EXAMPLE 10

Temperature Stability of Hemicellulase

An aliquot of broth was obtained from strain CMG1240 cultured in shake-flasks (48–72 hours at 35° C., pH 9.0) and clarified by centrifugation in a Microfuge. The supernatant was then filtered using a 0.45-micron filter; several aliquots were collected in sterile containers and stored on ice for use as controls. Some of these aliquots were subjected to steam sterilization for use as negative controls. The remaining supernatant was added to tubes and incubated in water baths maintained at 60° C. and 75° C., and in a 90° C. heating block. The activity of the enzyme at pH 9.0 and at these elevated temperatures over time was determined. The enzyme was stable at 90° C., exhibiting a half-life of 15 minutes in the absence of protecting agents. At 75° C., the enzyme reached 50% inactivation after 45 minutes. At 60° C., the enzyme reached 50% inactivation only after 5.5 hours. The results obtained in this experiment are presented in FIG. 2.

EXAMPLE 11

High Temperature Stability of Hemicellulase Formulated as a Lactose Powder

Figure 3:
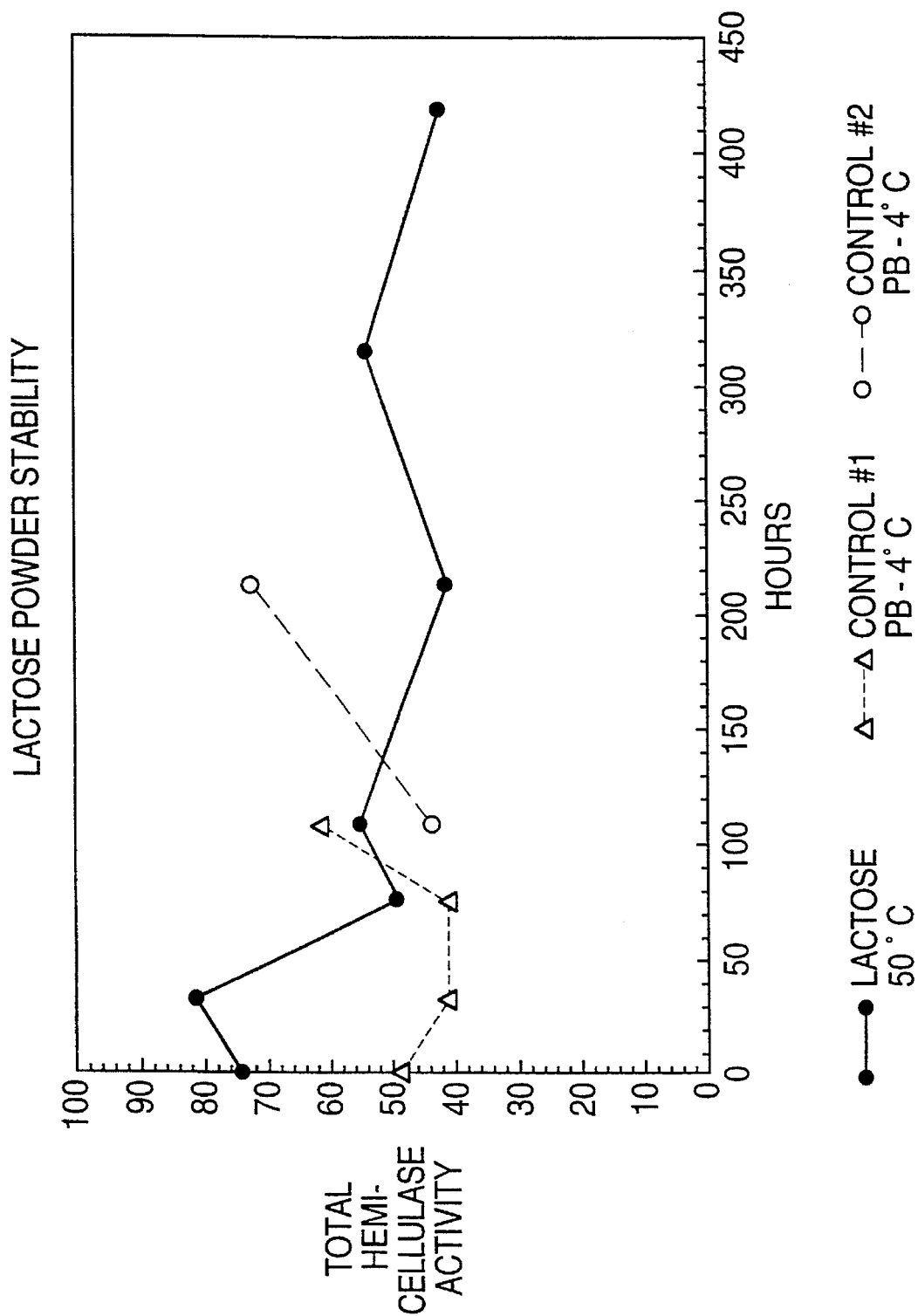
FIG. 3 shows the relative stability at 50° C. over time of a dried lactose formulation of the hemicellulase.

An aliquot of a hemicellulase solution prepared according to Example 8 (acetone precipitate) was extensively blended with 10 volumes (w/w) of powdered lactose. Two aliquots of the precipitate were dissolved in 10 mM phosphate buffer (pH 7.0) and stored on ice for use as controls. The dry lactose formulation was heated at 50° C. for more than 400 hours. The test results, as shown in FIG. 3, indicated that the lactose formulation showed virtually no loss of activity over the period tested.

EXAMPLE 12

Characterization of the Purified Hemicellulase

A broth concentrate was prepared by ultrafiltration, i.e., cells were removed with a 0.1-micron membrane and the enzyme concentrated with a 10,000 molecular weight cut-off membrane. When the enzyme became concentrated, it was observed that some of the hemicellulase passed through the membrane.

This permeate fraction was re-concentrated with the 10,000 molecular weight cut-off membrane and then used for further purification. The reconcentrated permeate was precipitated by the addition of three volumes of acetone at 4° C. The supernatant was siphoned off, and the precipitate resuspended in 50 mM phosphate buffer (pH 7.0) to a final volume of 222 mL. The enzyme concentrate was subsequently dialyzed against 10 mM phosphate buffer (pH 7.0) to remove any salts. The dialyzed concentrate was then applied to a DEAE-Sephacel column (2.8×30 cm). Elution of the hemicellulase was carried out by adding a solution of increasing ionic strength to the column at a flow rate of 1 mL/minute. The solution consisted of 0–1.25M NaCl in 50 mM phosphate buffer.

Ten-milliliter fractions were collected and tested for enzyme activity by measuring viscosity reduction of a 1% guar solution as described in Example 5. Fractions 96–109, which showed maximum activity, were pooled and then analyzed (along with molecular weight marker-proteins) on a 12.5% SDS-polyacrylamide gel. The results of this analysis indicated that the hemicellulase was highly purified, and had a molecular weight of 32,000. Hemicellulase fractions were ultimately purified by electrophoresis on the same type of SDS-gel and blotted onto Immobilon P PVDF membrane and stained with coomassie blue by the method of Matsudaira, *J. Mol. Biol.* 262: 10035–38. The hemicellulase band on the membrane was excised and used for amino acid sequence analysis. The enzyme was analyzed by Edman degradation using a Biosystems Gas Phase Sequenator. The N-terminal sequence of the purified enzyme was characterized as follows:

```
 1                    5                    10
Ala—Ser—Gly—Phe—Tyr—Val—Xxx—Gly—Thr—Ile—Leu—Xxx—

15                    20                    25
Asp—Ser—Thr—Gly—Asn—Pro—Phe—Lys—Ile—Xxx—Gly—Xxx—Asn
```

EXAMPLE 13

Percentage Relative Activity of Hemicellulase vs. pH

A hemicellulase preparation was prepared by admixing 30.0 lb Hydroxypropyl Guar per 1,000 gallons of 2% KCl in water. A 20 mL portion of the preparation was placed in a Brookfield viscometer UL cup. A control was prepared by adding 1 mL of deionized water to the 20 mL guar preparation. The viscometer cup was then stoppered and shaken. The cup was placed on the viscometer and dial readings were measured at 3 rpm for 10 minutes. Approximately 6 minutes were required to achieve stable readings.

Twenty-milliliter aliquots of the gel preparation were adjusted to various pH levels. One milliliter of broth from a shake flask as described in Example 2 was added to each aliquot. The dial readings measured at 3 rpm after 10 minutes were subtracted from the control dial readings. These differences were normalized relative to the results obtained at pH 7.0 at which maximum enzyme activity was observed. See Table II.

Figure 4:
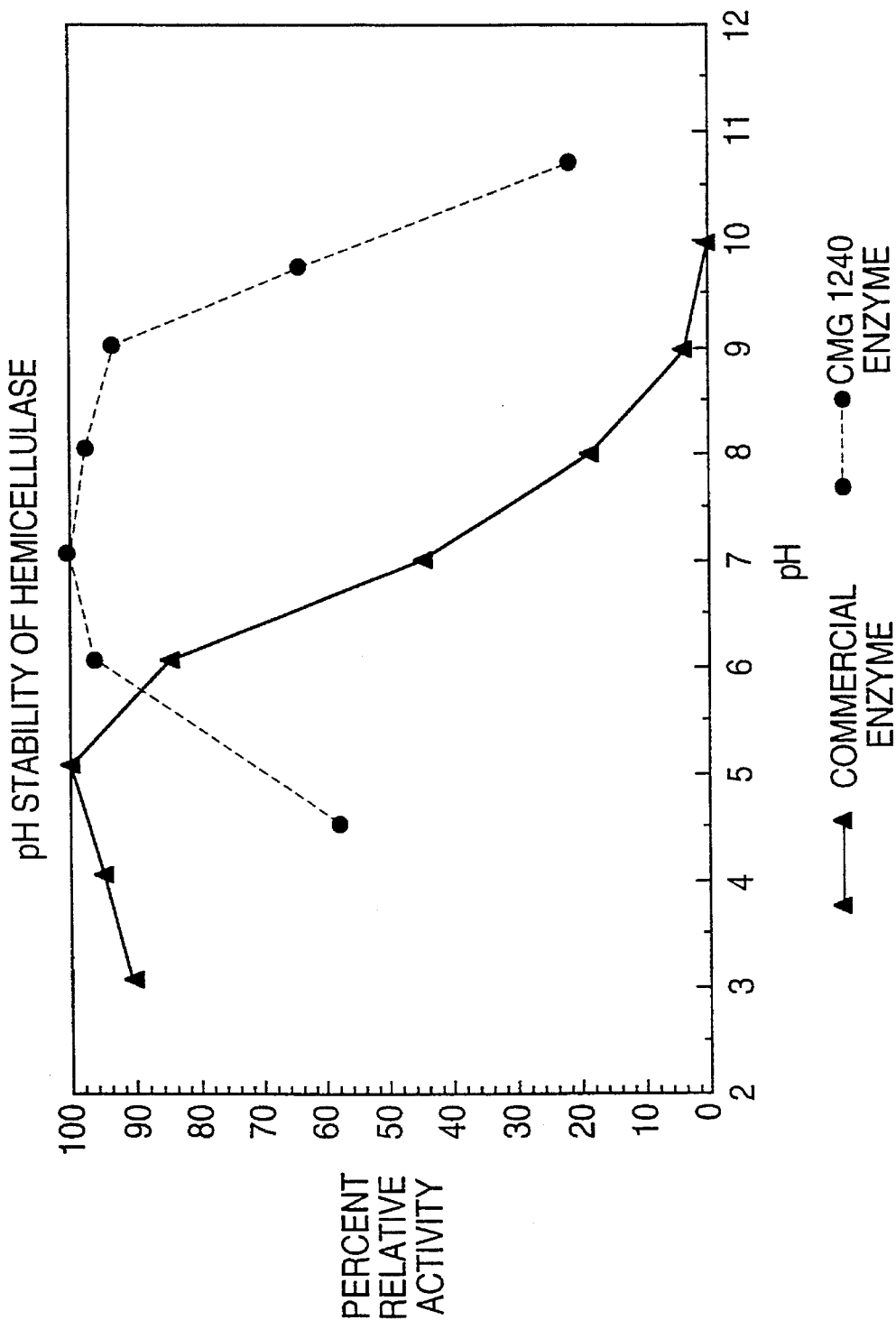
FIG. 4 is a graph that compares the pH profile of enzymatic activity for a hemicellulase of the present invention versus a known, commercially available enzyme.

The plot of relative enzyme activity vs. pH demonstrates that the enzyme displayed greater than 90% activity over a pH range of 6 to 9. FIG. 4 compares the activity of the enzyme vs that of a commercially available enzyme over a pH range of 2 to 11. The enzyme retained slightly more than 20% relative activity at pH 10.8.

TABLE II

% RELATIVE ACTIVITY OF HEMICELLULASE VS. PH

| pH | Dial Reading at 3 rpm | Control-Sample Differential* | % Relative Activity |
|---|---|---|---|
| 10.80 | 42.5 | 9.0 | 21.4 |
| 9.75 | 25.0 | 26.5 | 63.1 |
| 9.17 | 17.5 | 34.0 | 92.9 |
| 8.33 | 10.5 | 41.0 | 97.6 |
| 7.00 | 9.5 | 42.0 | 100.0 |
| 6.25 | 11.0 | 40.5 | 96.4 |
| 4.64 | 27.0 | 24.5 | 58.3 |

*Calculated by subtracting the dial reading of the sample from the dial reading (51.5) of the water control. Represents the loss in viscosity due to the presence of the enzyme.

EXAMPLE 14

Use of Hemicellulase Under Simulated Field Tests

A base gel was prepared by admixing the following in pounds per 1,000 gallons of 2% KCl in water:

40.0 lb Hydroxypropyl Guar 2.5 lb Fumaric Acid 10.0 lb Sodium Bicarbonate pH 7.4

The base gel corresponds to a commercial hydraulic gelling agent which would be used in the stimulation of a subterranean formation.

The base gel was admixed in a 4 liter Waring Blender for approximately 30 minutes after which time it was divided into 200 mL aliquots and permitted to further hydrate for at least 1 hour. Each sample was then further mixed with a variable speed laboratory stirrer equipped with a homogenizer blade for about 1 minute during which time the following were added to the fluid: 144 grams of sand (equivalent to 6 pounds per gallon concentration); enzyme formulated with lactose powder in a quantity identified below; and an organotitanate cross-linker in an amount sufficient to provide a concentration of 33 ppm $Ti^{+6}$. The base gel with additives was then placed in a heated bath maintained at 60° C. The viscosity of the cross-linked gel was measured with a Model 35 Fann Viscometer. The results, presented in Tables III and VI, demonstrate that a sufficient quantity of the hemicellulase will degrade cross-linked hydroxypropyl-guar fluid containing either sand or resin-coated sand.

TABLE III

20/40 Mesh U.S. Sieve Series, Ottawa Sand

| Time(hr) | Enzyme (lb/1000 gallons) Viscosity (centipoise) | | | | | | | |
|---|---|---|---|---|---|---|---|---|
| | 0 | 0.2 | 0.3 | 0.4 | 0.5 | 0.65 | 0.8 | 1.0 |
| 1 | C | C | C | 11 | 7 | — | — | 4 |
| 2 | C | C | WC | 8 | 5 | — | — | — |
| 4 | C | C | 12 | 8 | 5 | — | — | — |
| 6 | C | C | 10 | 7 | 5 | — | — | — |
| 22 | C | C | 8 | 6 | 5 | — | — | — |

C = Cross-linked; WC = Weak Cross-link; — = No Data

TABLE VI

20/40 Mesh U.S. Sieve Series, Resin-Coated Sand

| Time(hr) | Enzyme (lb/1000 gallons) Viscosity (centipoise) | | | | | | | |
|---|---|---|---|---|---|---|---|---|
| | 0 | 0.2 | 0.3 | 0.4 | 0.5 | 0.65 | 0.8 | 1.0 |
| 1 | C | C | — | — | C | C | WC | 24 |
| 2 | C | C | — | — | C | WC | 30 | 20 |
| 4 | C | C | — | — | C | WC | 20 | 10 |
| 6 | C | C | — | — | C | WC | 10 | 7 |
| 22 | C | C | — | — | C | WC | 7 | 6 |

C = Cross-linked; WC = Weak Cross-link; — = No Data

EXAMPLE 15

Activity of the Enzyme vs the pH of the Base Gel Preparation

A base gel was prepared by admixing the following in 1,000 gallons of 2% KCl in water:
40.0 lb Hydroxypropyl Guar
0.1 gallon ammonium/acetic acid buffer solution
10.0 lb Sodium Bicarbonate
The base gel was prepared according to the method described in Example 14 and maintained at 79.5° C. in a heated water bath. The viscosity of the base gel preparation was measured according to the method described in Example 14. The results are presented in Table V and VI.

TABLE V

HEMICELLULASE VS. BASE GEL PH (8.0–8.5)

| Time(hr) | Control | Dial Readings at 3 rpm | |
|---|---|---|---|
| | | 0.25 lb/1000 gal | 0.50 lb/1000 gal |
| 0 | 35 | 32 | 32 |
| 2.0 | 20 | 11 | 8 |
| 6.0 | 19 | 10 | 8 |
| 22.0 | 18 | 7 | 6 |
| Final pH | 9.1 | 8.8 | 9.1 |

TABLE V

HEMICELLULASE VS. BASE GEL PH (9.5–10.0)

| Time(hr) | Control | Dial Readings at 3 rpm | |
|---|---|---|---|
| | | 0.50 lb/1000 gal | 1.01 lb/1000 gal |
| 0 | 34 | 34 | 34 |
| 2.0 | 22 | — | — |
| 3.0 | — | 18 | 16 |
| 5.0 | 19 | — | — |
| 7.0 | — | 17 | 15 |
| 22.0 | 18 | 18 | 12 |
| Final pH | 10.1 | 9.5 | 9.5 |

What is claimed is:

1. In essentially pure form, the endo-β-mannanase enzyme purified from Bacillus strain CMG1240 having ATCC accession no. 55045 that catalyzes the degradation of mannan, wherein said enzyme
   (a) has a pH profile for endo-β-mannanase activity with the substrate guar that ranges from pH 4.5 to pH 11, and
   (b) retains 50% of its maximum activity after 45 minutes at pH 9.0 and 75° C. with the substrate guar.
2. An enzyme preparation comprising the essentially pure endo-β-mannanase enzyme according to claim 1.

* * * * *